United States Patent

Freij

Patent Number: 5,993,830
Date of Patent: Nov. 30, 1999

[54] COSMETIC SKIN PREPARATION

[75] Inventor: Göran Freij, Stockholm, Sweden

[73] Assignee: Ponsus AB, Stockholm, Sweden

[21] Appl. No.: 09/008,632

[22] Filed: Jan. 16, 1998

[30] Foreign Application Priority Data

Jan. 17, 1997 [SE] Sweden ................................. 9700129

[51] Int. Cl.$^6$ ................................. A61K 9/00; A61K 6/00
[52] U.S. Cl. ........................ 424/400; 424/401; 514/861; 514/886; 514/887; 514/937
[58] Field of Search .................................... 424/400, 401; 514/861, 886, 887, 937

[56] References Cited

FOREIGN PATENT DOCUMENTS

| | | |
|---|---|---|
| 0692238 A1 | 1/1996 | European Pat. Off. . |
| 0755668 A1 | 1/1997 | European Pat. Off. . |
| 2069333 | 8/1981 | United Kingdom . |
| 9602244 A1 | 2/1996 | WIPO . |
| 96022441 A1 | 2/1996 | WIPO . |

OTHER PUBLICATIONS

Junginger. Structure studies of stearate creams. Pharm. Ind. 46 (7), 758–762, 1984.

STN International, file CAPLUS, CAPLUS accession No. 1985: 12187, H. Junginger: "Structure studies of stearate creams".

STN International, File CAPLUS, CAPLUS accession No. 1995: 1006804, Kao Corp: "Foam–forming skin cleaners containing higher fatty acid salts".

STN International, File CAPLUS, CAPLUS accession No. 1996: 750672, Schneider, Ina–Maria et al: "Evaluation of drug penetration into human skin ex vivo using branched fatty acids and propylene glycol".

STN International, File CAPLUS, CAPLUS accession No. 1992: 645569, Takeuchi, Yoshikasu et al: "Effects of fatty acids, fatty amines and propylene glycol on rat stratum corneum lipids and proteins in vitro measured by Fourier transfrom infrared/attenuated total reflection (FT–IR/ATR spectroscopy".

STN International, File CAPLUS, CAPLUS accession No. 1992: 537579, Komata, Tasuko et al: "In vitro percutaneous absorption of thiamine disulfide from a mixture of propylene glycol and fatty acid".

STN International, File CAPLUS, CAPLUS accession No. 1987: 561540, Kaiho, Fusao et al: Application of fatty alcohols to pharmaceutical dosage forms. Part IV. Percutaneous absorption of indomethacin from mixtures of fatty alcohol and propylene glycol (FAPG bases) through rat skin effect of fatty acid added to FAPG base.

*Primary Examiner*—Thurman K. Page
*Assistant Examiner*—Lakshmi Channavajjala
*Attorney, Agent, or Firm*—Burns, Doane, Swecker & Mathis, L.L.P.

[57] ABSTRACT

The present invention relates to a skin preparation comprising lipophilic and hydrophilic components, which is intended for application on skin. The skin preparation according to the present invention is characterized in that it exists as a two-phase system and it is capable of creating a semi-permeable membrane in the skin. The invention also relates to a process for the manufacture of the skin preparation as defined above, which is characterized in that the lipophilic components are dissolved in water in a separate container to be combined with hydrophilic components, which have been blended and brought to react in another vessel. Finally, the present invention also relates to different uses of the skin preparation as defined above.

20 Claims, 1 Drawing Sheet

COSMETIC SKIN PREPARATION

This application claims priority under 35 U.S.C. §§119 and/or 365 to 9700129-1 filed in Sweden on Jan. 17, 1997; the entire content of which is hereby incorporated by reference.

1. Technical field

The present invention relates to a skin preparation comprising lipophilic and hydrophilic components for application on the skin. The skin preparation is effective against skin irritations, protects the skin against harmful substances and may also be used as a carrier. The invention also relates to a process for the manufacture of said skin preparation as well as the various uses thereof.

2. Background

Skin preparations have been used for a long time to render a softer and more elastic sensation to the skin. However, these days, we expose our skin in an increasing extent to a plurality of foreign substances, which in various degrees may be irritating and/or harmful. Of this latter reason, skin preparations are nowadays used more and more for a medicinal purpose than before. Also, the increased prevalence of allergies entails that more and more people experience contact dermatitis associated problems, which may be treated by application of some kind of ointment or other topical product.

Skin problems may appear on different parts of the body. For example, these days, the skin of the hands must withstand anything from within a range of strong detergents to dehydrating liquids, often combined with a mechanical impact. The skin of those occupied within certain professions is more exposed than that of others, especially as concerns the contact with chemicals. Infants using diapers frequently exhibit conditions of diaper dermatitis and people spending a lot of time in humid environments may have to treat their skin against dehydration. Skin problems may also arise in the knee areas, on feet etc., and the treatment thereof is often inevitable.

Conventionally, to protect the skin from harmful substances, a classical kind of skin preparation denoted barrier ointments have been used. The purpose of these is to provide a film on the skin and thereby create a layer, which is impermeable to external irritants. Thus, this kind of ointments rely on the principle of occlusion, which means that a covering layer is provided on the skin, thereby constituting a certain degree of protection as long as it remains in place. Accordingly, even a very small mechanical influence, such as e.g. may arise because of contact between the skin and clothes etc., will remove the layer of ointment and thereby eliminate the protecting barrier. Other disadvantages of the barrier ointments are that they, due to the impermeability thereof, both increase the body temperature of the user and prevent perspiration, which in turn may render an uncomfortable sensation to the user thereof. Another disadvantage with the barrier ointments is that they often exhibit a better performance in regard of some substances than others. Consequently, there may be a need of different preparations adapted for different substances, which the user may contact. Naturally, this is most impractical in most situations as it is then required to know more specifically what kind of protection there will be a need of.

Another way of protecting the skin of the hands is simply to use plastic or rubber gloves. However, in some instances, this is most impractical and awkward and it may even be unhealthy during extended periods of time, since the inside of the plastic glove easily becomes humid because of the body heat of the user. In addition, not even plastic gloves will provide a satisfactory protection in certain cases, as some substances, such as e.g. solvents, are capable of diffusing through the plastic and/or rubber and thus contact and penetrate the skin. Finally, another disadvantage of the use of gloves is the allergies often evoked by the glove material.

SUMMARY OF THE INVENTION

The present invention solves the problems defined above by providing a skin preparation, which is capable of forming an osmotic, i.e. semi-permeable, membrane in the skin. The osmotic membrane will protect the skin against influences of harmful substances. In addition, it will furnish the skin with an improved ability to recover from any defects. The skin preparation according to the invention comprises both lipophilic and hydrophilic components present therein as two phases. Thanks to the two phases the skin preparation will act simultaneously on several levels in the skin. Thereby, it will enhance the inherent properties of the skin rather than simply supply substances to the skin to order alleviate symptoms, like the conventional skin ointments.

BRIEF DESCRIPTION OF THE DRAWINGS

FIG. 1 shows untreated human skin in a magnification of 600×, clearly disclosing impaired cell membranes with marked speces in between.

DETAILED DESCRIPTION OF THE INVENTION

Figure 1:
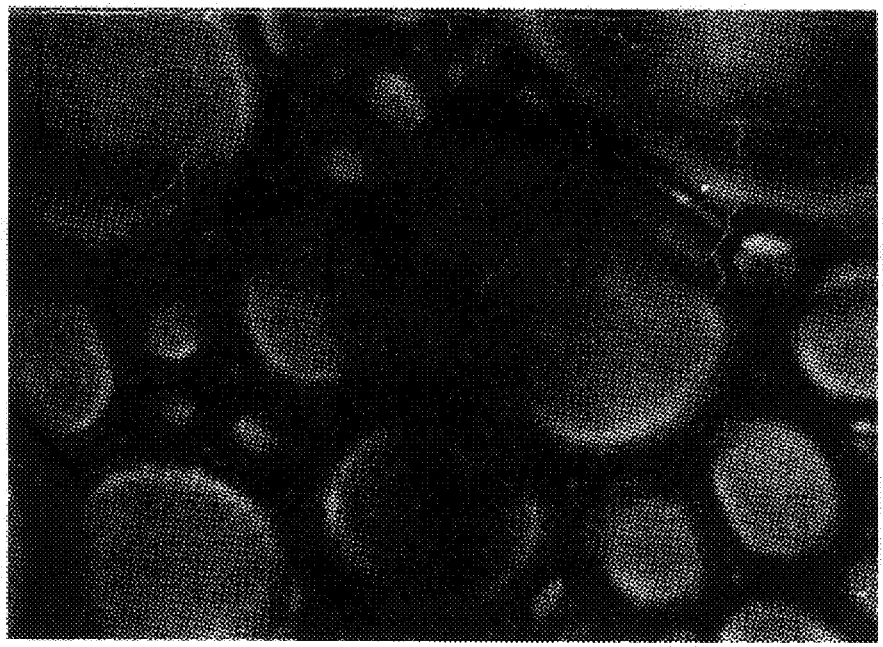

Accordingly, the present invention relates to a skin preparation for topical application on the skin. The skin preparation comprises lipophilic and hydrophilic components in a two phase system, whereby it is capable of creating an osmotic, i.e. semi-pereamble, membrane in the skin. Thus, the skin preparation according to the invention constitutes a two-dimensional filter membrane, whereby a totally new mode of action is achieved. The lipophilic components of the skin preparation will prevent any immediate contact between water and water soluble substances and the treated skin's hydrophilic parts, which, thus, will prevent dehydration of the skin. In addition, when used, hydrophilic centra will arise in the lipophilic regions in a such a way so that the normal perspiration is practically not influenced at all. This will advantageously prevent any increase of the temperature of the skin due to the use of the present skin preparation. In the present application, the term "osmotic membrane" is intended to mean such a semipermeable membrane as the ones the cell walls of normal, healthy living organisms constitute. As the skin preparation according to the present invention creates and regenerates such an osmotic membrane, the inherent capability of the skin to maintain a balance between outflow and inflow of, inter alia, humidity and heat, will be maintained and/or re-established. It is assumed that the skin preparation according to the present invention will aid and enhance the skin in more ways than only the clear protecting function, thereby creating a healthier skin with close to optimal advantageous native properties.

Thus, in the first aspect thereof, the present invention relates to a skin preparation prepared from lipophilic as well as hydrophilic components. In one preferred embodiment, the lipophilic components are chosen among fatty acids with fourteen to twenty carbon atoms or any mixtures thereof and dimethylpolysiloxane (dimethicone), the hydrophilic components being chosen among triethanolamine, monopropylene glycol, glycerol, sorbitol, polyethylene glycol and polyvinyl pyrrolidone.

In one preferred embodiment, the skin preparation according to the invention is prepared from one lipophilic component comprising said fatty acid or a mixture thereof, and one hydrophilic component comprising triethanolamine, the molar ratio of fatty acid (mixture): triethanolamine preferably being higher than 1.

In another preferred embodiment, the skin preparation according to the present invention is prepared from one lipophilic component, which is a mixture of fatty acids of the following composition: at most about 2% of a component consisting of a chain of fourteen carbon atoms, between about 47 and about 52% of a component consisting of a chain of 16 carbon atoms, between about 43 and about 48% of a component consisting of a chain of 18 carbon atoms and at most about 1% of a component consisting of a chain of twenty carbon atoms. All percentages given in the present application are indicated in weight/weight.

In one alternative embodiment, said fatty acid consisting of a chain of fourteen to twenty carbon atoms, or said mixture of such fatty acids, may be of any other composition, for example containing an essential portion of myristic acid, such as about 90% myristic acid or an essential portion of palmitic acid, such as about 90% palmitic acid. Thus, in the present context "a fatty acid consisting of a chain of fourteen to twenty carbon atoms, or a mixture of such fatty acids", refers to any suitable mixture of higher fatty acids. However, a predominant portion of a fatty acid consisting of a chain of 18 carbon atoms is most preferred.

Thus, the most preferred embodiment of the skin preparation according to the present Invention is prepared from a ratio between a fatty acid mixture, having the above defined preferred composition, and triethanolamine higher than about 2:1, preferably higher than about 3:1. Other advantageous embodiments of the skin preparation according to the present invention are prepared from the same ratio between any equivalent lipophilic component and triethanolamine.

Thus, according to the present invention, it has been shown to be advantageous to adapt the ratio between the primary lipophilic components, i.e. the fatty acid consisting of a chain of 14 to 20 carbon atoms or the mixture of such fatty acids, preferably of the above defined composition, and triethanolamine to enable a certain portion of the acid in the final skin preparation to form a salt with the triethanolamine, while another portion exists as free fatty acid. The presence of both the free fatty acid and the salt in the final product, resulting from the above defined preferred ratios between the mixture of fatty acids and the triethanolamine, may be one reason to the unique properties of the skin preparation according to the invention, i.e. that it acts both in the depth of the skin and creates the osmotic membrane, which is new per se, and, additionally, that it simultaneously is capable of protecting the surface of the skin against influences of deleterious substances. These specific properties of the skin preparation according to the invention are also presumably due to the particular method of preparation thereof, which will be described in more detail below.

In one particular embodiment, the skin preparation according to the invention is prepared from a fatty acid consisting of a chain of 14 to 20 carbon atoms, or any mixture of such fatty acids, triethanolamine, monopropylene glycol, polyvinyl pyrrolidone, dimethyl polysiloxane and a component which is chosen among glycerol, sorbitol, and polyethylenglycol, or a mixture thereof, as well as water.

As concerns the choice of glycerol, sorbitol or poylvinyl pyrrolidone, the primary purpose of this component is to enable the skin preparation according to the invention to be quickly absorbed by the skin. In general, the component will reside in the more humid parts of the horny layer of the epidermis. In a simple embodiment thereof, the skin preparation according to the invention is prepared from glycerol, whereas in alternative native embodiments it is prepared from sorbitol or polyethylene glycol, such as PEG 200, in equivalent amounts. In other embodiments, the skin preparation according to the invention is prepared from a mixture of MPG sorbitol and PEG or any other suitable mixture of the above defined components.

As regards the ingredients used in the manufacture of the skin preparation according to the present invention, some suitable examples thereof are as follows. The triethanolamine mine may e.g. be 99LFG85 (MB-Sveda), the fatty acid component may e.g. be Safacid 16/18CR$^R$ (Vendico Chem) and the polyvinyl pyrrolidone may e.g. be PVP K30 (ISP).

As a result of the composition defined above, the skin preparation according to the invention will not supply any grease to the skin and therefore it is totally non-sticky, which renders a much more comfortable sensation to the user than the conventional skin preparations do, often leaving a sticky alyer behind.

One preferred embodiment of the skin preparation according to the invention is prepared from about 5 to 8% of a fatty acid consisting of a chain of 14 to 20 carbon atoms, or a mixture of such fatty acids, e.g. the preferred mixture defined above, about 0.73–2.66% triethanolamine, about 4.5–7.0% monopropylene glycol, about 1–2.5%, preferably 1.5–1.97% polyvinyl pyrrolidone, at most about 5%, such as about 1–2.5% and preferably about 0,5–0.95%, dimethyl polysiloxane and about 1.5–2% glycerol, sorbitol or polyethylene glycol, or any mixture thereof, the balance being water up to 100%. According to an especially advantageous embodiment, the skin preparation according to the invention is prepared from about 6.25% of a fatty acid consisting of a chain of 14 to 20 carbon atoms, or any suitable mixture of such fatty acids, e.g. the preferred mixture as defined above, about 0.91% triethanolamine, about 5.8% of monopropylene glycol, about 1.96% polyvinyl pyrrolidone, about 0.89% dimethylene glycol and about 1.52% of glycerol, sorbitol or polyethylene glycol, or any mixture hereof, the balance being water. As regards the portion of dimethyl polysiloxane, it is noted that even though the preferred percentages are as indicated above, it may be any value within the region of from 0% and up to about 5%, depending on the other ingredients.

The skin protection according to the invention is prepared from polyvinyl pyrrolidone (PVP), a preferred average molecular weight being about 8,000–63,000 Dalton, preferably about 38,000 Dalton. The dimethyl polysiloxane (dimethicone), which the skin preparation according to the invention is prepared from, exhibits an exemplary viscosity of from about 100–1,000 cp, preferably about 350 cp. Anyway, the polymers from which the skin preparation according to the invention is prepared will exhibit a high enough level of polymerisation not to penetrate the horny layer of the epidermis of the skin.

In one embodiment, the skin preparation according to the invention includes a frothing agent, e.g. Polysorbate 20. If present, said frothing agent is used in an amount of about 1.3–2.7%, preferably about 1.5%.

In another embodiment, the skin preparation according to the invention comprises a preservative and/or an aromatic agent, the preservative being present in an amount of about 0.5% and the amount of the aromatic agent being about 0.05%–0.5%, preferably about 0.18%. However, said amount is dependent upon the kind of aromatic agent chosen. One preferred preservative according to the invention is Phenonip, which is well known within this field.

In the most preferred embodiment of the skin preparation according to the invention, the two phase skin preparation according to the invention is prepared to enable application thereof as a foam, for example, from an aerosolic container. The choice of propellant added to create such a product will be dependent on the intended use and may easily be done by a person skilled within this area. Typically, and contrary to the present skin preparation, the prior art preparations that comprise both lipophilic and hydrophilic substances are emulsions. The skin preparation according to the invention is, however, composed of two phases, which preferably are blended together, and not emulgated, when applied on the skin. Thus, in addition to the above defined advantages of the skin preparation according to the invention, one further advantage is that it is both easier and cheaper to manufacture than an emulgated preparation, since the manufacture of an emulsion will demand for a very powerfail agitation and, accordingly, a large consumption of energy. The manufacture of the skin preparation according to the invention will be disclosed in more detail below.

In a second aspect, the present invention is a process for the manufacture of a skin preparation comprising lipophilic and hydrophilic components. More specifically, a skin preparation that enables the forming of an osmotic or semi-permeable membrane in the skin, such as the skin preparation disclosed above. In its simplest embodiment, the process is characterized by the following steps:

a) the dissolution in water of a fatty acid consisting of a chain of 14 to 20 carbon atoms, or a mixture of such fatty acids, in a vessel during careful agitation to provide Solution A;

b) the dissolution, in another vessel, of polyvinyl pyrrolidone in water and during powerful agitation;

c) the addition, during agitation, of monopropylene glycol, triethanolamine and glycerol, sorbitol or polyethylene glycol, or any mixture of those three last mentioned; to the product obtained from step b), whereby Solution B is obtained after a reaction time $t_c$;

d) the feeding of Solution B to the vessel containing Solution A, whereafter the contents thereof are allowed to react during a reaction time $t_d$; and, e) the cooling of the product from step d) by the addition of cold water during continued agitation, the dimethylpolysiloxane being added and the total amount being balanced with water.

According to one particular embodiment of the process as defined above, a frothing agent, an aromatic agent and/or a preservative are also added, preferably together with the dimethyl polysiloxane. These further additives may be of different kinds, proportions and amounts, such as the ones already disclosed above in connection with the skin preparation according to the invention.

According to an advantageous embodiment, step a) and/or step b) of the process are performed at a higher temperature than about 80° C., such as about 95° C. According to an advantageous embodiment, the above defined times $t_c$ and $t_d$ are about 30 minutes and 60 minutes, respectively.

The process according to the invention may be performed in any conventional vessel, while step b), however, preferably is performed in a high speed double-mounted turbine dissolver. The agitation is provided e.g. by a propeller. As concerns other measures, equipments, reagents etc. in connection with the process according to the invention, a person skilled within this area will easily make the requisite choices and judgements thereof to achieve the desired results.

According to one embodiment of the process according to the invention, a mixture of fatty acids consisting of chains of 14 to 20 carbon atoms is used, which exhibits the following composition: at most about 2% of a component consisting of a chain of 14 carbon atoms, between about 47 and about 52% of a component consisting of a chain of 16 carbon atoms, between about 43 and about 48% of a component consisting of a chain of 18 carbon atoms and at most about 1% of a component consisting of a chain of 20 carbon atoms. Alternative compositions of said mixture of fatty acids consisting of chains of 14 to 20 carbon atoms are already mentioned above in connection with the skin preparation according to the invention.

In an advantageous embodiment, the process according to the invention relates to the manufacture of a skin preparation, which comprises about 5 to 8%, preferably about 6.25%, of a fatty acid of 14 to 20 carbon atoms, or a mixture of such fatty acids, about 0.73% to 2.66%, preferably about 0.91% of triethanolamine, about 4.5 to 7.0%, preferably about 5.8%, of monopropylene glycol, about 1–2.5%, such as about 1.5 to 1.97%, preferably about 1.69%, of polyvinyl pyrrolidone, anywhere between 0 and 5%, such as about 0.5 to 0.95%, preferably about 0.89%, of dimethyl polysiloxane and about 1 to 2%, preferably about 1.52%, of a component, which may be anyone of glycerol, sorbitol and polyethylene glycol, or any mixture thereof, the rest being balanced with water up to 100%. Specifically preferred ratios between the lipophilic and hydrophilic components are as already discussed above in connection with the skin preparation according to the invention.

In a third aspect of thereof, the present invention relates to a method of treatment for alleviating or preventing itching and/or other skin irritation, such as contact dermatitis, eczema etc., in an animal in need thereof, including humans, which comprises the application on the skin of a skin preparation according to the invention in an amount suitable for the intended purpose. The method according to the invention is superior to the use of conventional skin ointments, inter alia as the skin preparation according to the invention will penetrate further into the skin. Consequently, it will produce a more profound effect than any one of the prior art skin ointments. Meanwhile, the skin preparation will provide a protection on the skin surface which resembles the protection from a barrier ointment, however, without entailing any sticky or otherwise compromising layer on the skin. Moreover, and surprisingly, it has the been shown that the advantageous effects of the skin preparation according to the invention remains during an extended period of time, even after washing of the skin. This native osmotic protection obtained by the invention has never before been possible to obtain by the application of a topical preparation.

Surprisingly, the skin preparation according to the invention has been proven useful as a protection even against corroding substances, such as concentrated acids.

The skin preparation according to the invention may also be used in treatment and/or protection against the metal nickel. This is of great interest, as nickel allergies are increasing steadily, partly due to the use thereof in jewellery, especially in earrings. Up to now, no topical skin preparation has existed capable of protecting against and preventing nickel allergies. The only known treatment have been applying some kind of physical protection, such as clothing, or a barrier ointment, which naturally is no alternative when it comes to nickel containing jewellery. Thus, the capability of protecting against Ni is one of the many new and advantageous effects of the skin preparation according to the invention.

One particular use of the skin preparation according to the invention may also be as a carrier, for example to carry a substance active as a medicament. However, the skin preparation according to the invention may also be used as a carrier of any other substance. Examples of substances which may be carried in a skin preparation according to the invention are sunscreens and sun filtering agents, surface anaesthetics, fungicidal agents, bactericides etc. Accordingly, the present invention also relates to a method of treatment of a human or animal body comprising the application of a skin preparation according to the invention comprising an active agent to treat and/or prevent diseases or other compromising conditions, such as sunburn, itching, rashes etc. The advantages of the administration of an active substance by the use of the present skin preparation over conventional routes for administration, such as oral preparations, or in adhesive plasters or bandages containing the active substance, are several. For the topical administration through the skin, an adhesive plaster will after repeted administrations result in a substantial irritation of the skin, which may be painfull and, finally, may even lead to infections. Contrary, the present skin preparation is capable of administering the active substance to profound depths of the skin and will keep the skin soft and healthy meanwhile. Different propellants may be used depending on the intended use of the preparation, such as propane or butane. However, at present, there are indications that butane, or a mixture wherein butane is predominant, is the most advantageous propellant, even though other equivalent alternatives may be used if deemed suitable for a particular aplication. A person skilled within this field may well make an appropriate choice of a suitable propellant for each situation and application.

According to the a preferred embodiment of the above defined method, the skin preparation is applicated on the skin a repeted number of times, e.g. every fourth to sixth hour, such as every fifth hour. In some instances, it may be more advantageous to use the skin preparation according to the invention by repeating the above given frequency of application during one or several weeks, such as one to five weeks.

Detailed Description of the Drawings

FIG. 1 shows untreated human skin in a magnification of 600×, clearly disclosing impaired cell membranes. The gaps between the cells are evident, evidently showing a skin which is not healthy and thus does not possess its natural properties to heal and protect the organism from foreign substances.

Figure 2:
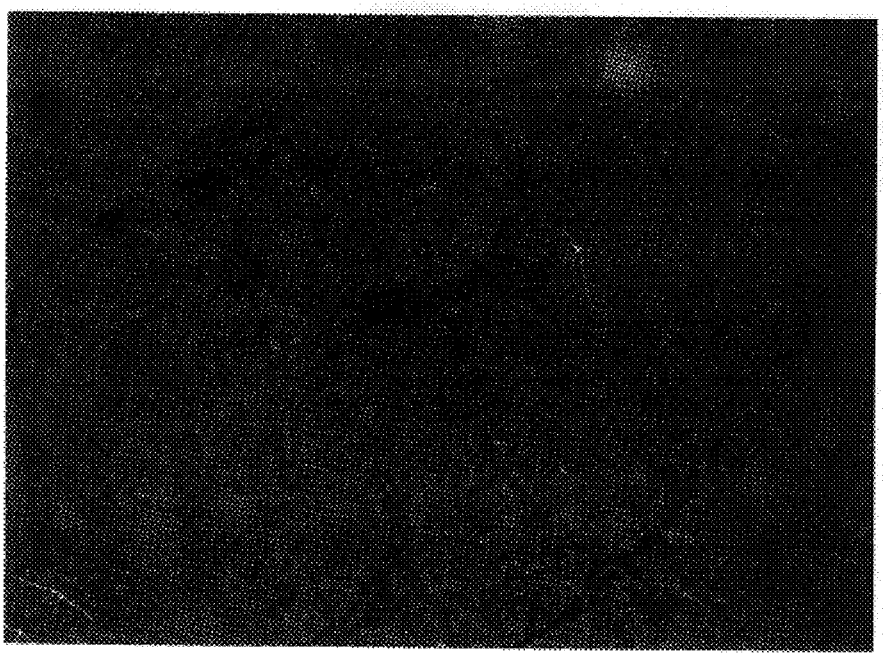
FIG. 2 shows a human skin, which, 45 minutes before the picture was taken, was treated with a skin preparation according to the invention, in a magnification of 150×.

FIG. 2 shows a human skin, which, 45 minutes before the picture, was treated with a skin preparation according to the invention, in a magnification of 150×. The cell membranes have now been strengthened. Conclusively, the treated skin appears as more coherent, which indicates that the skin possesses cell membranes that have regenerated their native semi-permeable, or osmotic, membranes.

EXAMPLES

Below, examples of the skin preparation according to the invention are disclosed by the ingredients and manufacture thereof. Also, the advantageous results of several tests performed at institutions acknowledged within this area are reported. In the experimental descriptions that follows, references are sometimes made to complete reports produced by the institution in question, which reports are hereby incorporated herein by reference. It is stressed that these examples are only construed to illustrate the invention and that thay are not to be interpreted as limiting the scope of protection as defined by the claims in any way.

Preparation, Example 1

A skin preparation was prepared from the following ingredients in the amounts indicated below:

| Ingredient: | amount, % (w/w) |
|---|---|
| Stearic acid | 6,56 |
| Monopropylene glycol (MPG) | 6,09 |
| Polyvinyl propylene (PVP) | 2,0 |
| Glycerol | 1,78 |
| Polysorbate 20 | 1,78 |
| Triethanolamine (TEA) | 1,1 |
| Dimethicone | 0,95 |
| Preservative | 0,5 |
| Water | to 100 |

Process of Preparation

Phase 1 is prepared by warning about ⅓ of the water to about 95° C. in a vessel equipped with propeller agitation. The steraric acid is added to the water during agitation.

Phase 2 is prepared by dissolving PVP in water at a temperature of about 95° C., in a double mounted turbine dissolver during energetic agitation. Then, MPG, glycerol och TEA are added and the mixture is blended during about 30 minutes.

Phase 2 is then supplied to Phase 1 and the two phases are agitated during 1 h. The mixture is cooled by the addition of cold waterduring continued agitation. Finally, Polysorbate 20 and a preservative (Phenonip) are added, The total amount is balanced up to 100% by the addition of water.

The resulting liquid product including the two phases is blended with a requisite amount of a suitable propellant and it is supplied to a suitable aerosolic container, from which the skin preparation may be withdrawn as a foam. Its non-sticky character and the foam form makes it easy to distribute over the desired area of skin and pleasent to wear.

Preparation, Example 2

Below, the best mode of the skin preparation according to the invention is disclosed, as is known by the inventor at the filing of the present application. Thus, a skin preparation was prepared from the following ingredients in the amounts indicated below:

| Ingredient: | Amount, % (w/w) |
|---|---|
| Stearic acid | 6,25 |
| Monopropylene glycol (MPG) | 5,8 |
| Polyvinyl propylene (PVP) | 1,9 |
| Glycerol | 1,7 |
| Polysorbate 20 | 1,4 |
| Triethanolamine (TEA) | 1,05 |
| Dimethicone | 0,95 |
| Preservative | 0,5 |
| Water | to 100 |

Process of Preparation

The present skin preparation was prepared as disclosed above in example 1. A soft and pleasent foam was obtained, which is excellent for use to treat skin irritations and rashes. It is also suitable to use as a carrier of an active substance, e.g. UV absorbants in order to create a sun screen preparation. Examples of other active substances may be any substance that have a pharmaceutical effect and, thus, the present preparation may be used for a topic administration of medicaments.

In addition, the present skin preparation also made the skin on which it was applicated resistent to concentrated sulphuric acid. Thus, said acid could be contacted with the hands treated with the skin preparation without causing any disagreeable feeling or lesion.

Preparation, Example 3

A skin preparation was prepared from the following ingredients in the amounts indicated below:

| Ingredient: | Amount, % (w/w) |
| --- | --- |
| Stearic acid | 7,8 |
| Monopropylene glycol (MPG) | 6,8 |
| Polyvinyl propylene (PVP) | 1,5 |
| Glycerol | 1,0 |
| Polysorbate 20 | 1,34 |
| Triethanolamine (TEA) | 1,9 |
| Dimethicone | 0,5 |
| Preservative | 0,5 |
| Water | to 100 |

Process of Preparation

The present skin preparation was prepared as disclosed above in example 1. A soft foam was obtained, which was easily absorbed by the skin and pleasent to wear. The skin felt flexible after application thereof, especially after a repeted use.

Test No. 1: Tolerance of the Protective Foam Used to Substitute Latex Gloves

This test was performed at Forensic Medicine, Siemens, Munchen (ref. doc. 1–4)

The aim of this test was to evaluate to what extent the skin preparation according to the invention could replace latex gloves. 3 subjects participated in the study, two women and one man. The effect of a preparation according to the invention on the hands of the subjects was evaluated after one, two and several days of use. The enhancement of the symtoms were studied and an evaluation was made.

The test subjects were divided into the following groups:
1) Hands washed frequently, leading to a dry and crisp skin
2) Neurodermatitis, "bloody eczema"
3) Frequent hand washing, eczema Results—Conclusions

| Overall appreciation | of the patient: | of the physician: |
| --- | --- | --- |
| 1. Softened skin | very good | very good |
| 2. Improvement, no bloody exfoliations | good | good |
| 3. Improvement judged as prophylactic | very good | very good |

Test No. 2: Protective Foam According to the Invention in Professional Skin Injuries The present study was performed at General Motors, Austria (ref. p. 29–33)

The aim of this study was to evaluate the protective capacity of a skin preparation according to the invention in professional skin injuries. 58 test subjects participated in the test, 55 of which were women and 3 of which were men.

The skin preparation was applied daily as a foam. The evaluation of the effect thereof was made by observation of skin injuries visible to the naked eye.

The test subjects were grouped as follows: Subjects with injuries on the hands and forearm resulting from the use of corrosive agents in professional environment. Subjects with toxic hand eczema.

Results—Conclusions

Satisfactory results in general.

36 subjects have judged the result very good.

15 subjects have judged the result as good.

1 subject has judged the result as moderate.

6 subjects have judged the result as null.

Test No. 3: Protective Capacity of the Protective Foam in Cases of Severe Skin Irritations This study was performed at "Manufacture of treatment of metals", Eppelheim (forensic medicine).

The aim was to evaluate the improvement of clinical symtoms of intolerance that may be obtained by the skin preparation according to the invention. In the study, in total 12 test subjects participated, all of which were men exhibiting severe skin irritations. A preparation according to the invention was applied as a foam on the skin of the test subjects. Thereafter, the state of the skin and the elasticity thereof as well as the disappearance of chaps, desquamation and the itching was studied after 1, 2 and several days of treatment.

Results—Conclusions

Convincing results in 10 patients (good to very good evaluation) out of 12. 1 subject without any improvement (one of the last 12).

Test No. 4: Activity of the Protective Foam in Professional Skin Symptoms

This study was performed at Photochemistry firm (Nussloch) (ref. p. 59–69).

The aim was an assessment of the improvement in the professional skin symptoms in the acceptability of the skin preparation according to the invention. Ten test subjects participated (8 males and 2 females). The test period was 3 weeks. Subjects were chosen since they were involved in handling of chlorinated hydrocarbons and were suffering of skin injuries.

An evaluation was made of improvement in skin condition, symptoms and skin elasticity.

Results—Conclusions

| Overall appreciation | of the patient: | of the physician: |
| --- | --- | --- |
| Moderate | 1 | 1 |
| Very good | 4 | 4 |
| Good | 4 | 5 |
| None | 1 | 0 |

Test No.5: Protective Capacity of the Protective Foam in Professional Dermatititis The present study was made at Forensic Medicine Bauer & Shaurte Karcher SARL, Neussynhein (ref. p. 81–88).

The aim was an assessment of the improvement in the professional dermatosis. The test involved 7 test subjects, 3 men and 4 women, suffering from professional dermatosis.

The test subjects applied a preparation according to the present invention on the skin, then skin elasticity, reduction in pain, desquamation, pruritus and redness were evaluated.

Results—Conclusions

| Overall appreciation | of the patient: | of the physician: |
|---|---|---|
| | Very good | Very good |

Test No. 6: Recurring Contact Eczema

This study was performed at the "Dermato-veneriology surgery"(Trier) (ref. p. 89–92).

The aim was to evaluate the protective capacity of the foam according to the invention in wine growers experiencing recurring chronic contact eczema. In the study, 10 wine growers participated (4 men, 6 women). The test subjects applicated the preparation on their skin.

The preparation according to the invention was judged both of the patients and of the physician as regards tolerance and efficiency.

Results—Conclusions

The physician has judged the result as excellent in 10 cases. The patients have judged the result as very good in 7 cases and good in 3 cases.

Test No. 7: Skin Allergy

The present study was performed at the Forensic medicine (SARL SCOCA Weid-müller DETMOLD) (ref. p. 99–101).

The aim was to assess the effectiveness of a skin preparation according to the invention as a protecting preparation. The test included 6 subjects suffering from neurodermatitis, contact allergy, food allergy, skin sensitivity to cleansing products. A skin preparation according to the invention was applicated as a foam and then the improvements of the symptoms were judged.

Improvement in skin elasticity, skin reactions (burning sensation, itching), allergies (redness and pruritus) were evaluated.

Results—Conclusions

Increased skin elasticity, disappearance of the skin reactions and allergies.

Test No. 8: Skin Irritation and Capacity of Allergenic Sensitisation

This study was performed according to GLP at the Research & Consulting company AG, Itingen, Switzerland (ref to report no. 200114, p. 243–284).

The aim was to study the effect of application on the skin of a protecting skin preparation according to the invention as regards skin irritation and allergy. The test included 30 guinea pigs (Himalayan white spotted guinea pig; 15 males, 15 females, weighing 449–485 and 411–476, respectively).

The Dosage Was as Follows:

Skin application. Dose:

(1) induction (from D0 to D28), daily applications of 0.025 ml of undiluted product to a skin area measuring 2 cm$^2$, 5 days a week;

(2) challenge (from D35 to D42), application of 0.025 ml of undiluted product to a skin measuring 2 cm$^2$.

The test was performed according to (1) OECD Guideline No. 406, 1981: "Skin sensitisation" and (2) Directive 84/449, EEC, B.6: "Acute toxicity—Skin Sensitisation", and (3) Pesticide Assessment Guidelines of US Environmental Protection Agency, paragraph 81.6 (study of skin sensitisation).

The method used was obtained from Dermatoxicology, Ed F. N. Marzulli & H. J. Maibach, 1982, Hemisphere Publ., chapter 9, author G Klecak, pp 213–219.

The Following Principle Was Used:

(1) Single or repeated application of the test product on the animal in order to induce a hypersensitivity.

(2) Rest period after this application in order to favour the development of the hyper-sensitivity in the animal.

(3) Single or repeated application, at the end of the induction, of the test product on the animal in order to reveal possible sensitisation reactions.

(4) Quantitative assessment of the sensitisation reactions (at least, for the erythematous and oedematous reactions).

The product is considered as allergenic for a certain concentration (non irritant), if at least one animal of the group has positive reactions.

Results:

No difference was observed between the treated and the control groups after the first and second challenges. The protective foam for topical use has proved not to have any capacity of allergenic sensitisation in the albino guinea pig.

Test No. 9: Assessment of Skin Protective Properties

This study was performed according to GLP at Scantox, Biological Laboratory Ltd, 40 Tombjervej, P O Box 28, DK-4623 Lille Skensved, Denmark (ref. to Report no. 10662, pp. 10–19).

The aim was to evaluate the skin protecting properties of the topic preparation according to the invention. The test included 8 female albino rabbits of "Chbb": HM, CH Boehringer/Biberach. "Himalaya" strain from Dr Karl Thomae GmbH, D-7950 Biberach and der Riss. The weight of the rabbits were 1.9–2.3 kg.

The method used was an unofficial method of which the principles are drawn from OECD Guideline No. 404, 1981 "Skin Acute Irritant/Corrosive Effect"

The following principle was followed: Application of the test product on the previously clipped skin. 5 minutes later, application of a gauzepack drenched with a solution of 60% sulphuric acid for 1, 2, 4, 6, 8 minutes. Observation and notation of the effects induced by the acid according to numerical scale 30 minutes later and then, 4, 24, 48 and 72 hours later, to appreciate the reversibility of the observed injuries.

Results:

The pre-treated skin resists to the effects of the application of the acid during 4 minutes versus only 1 minute for the control skin.

Test No. 10: Protective Properties Against Brucellosis

This test was performed according to GLP at Bouisson Bertand Institute, National Centre of Reference on Brucella, Faculté de Médicine, rue de la Croix-Verta, F-34090 Montpellier, France (ref. pp. 337–345).

The aim was to evaluate a topic use of a protective foam according to the invention in regard of Brucellosis. The test comprised two parts, a preliminary test and an infection test. Each test comprised 20 Swiss mice (10 controls +10 treated).

The Following Principle Was Followed:

Preliminary test: application of the test product on a skin area measuring about 1 cm$^2$. deposit of a culture of *Brucella melitensis* M15 alive on the treated area. After 4 hours of contact, the product is removed (without using soap). Research of Brucella on the skin using a seeding on a solid Albimi medium of samples taken with a cotton swab.

Infection test[1] (experimental brucellosis): application of the test product on a skin area measuring about 1 cm$^2$ of a previously scarified zone. three hours later, deposit of a culture of *Brucella melitensis* M15. observation of the mice during 15 days, then sacrifice and necropsy. Research of an infection using cultures of homogenised liver and spleen on a solid Albimi medium.

The Test Animals Were Prepared as Follows:

Preliminary test: depilated mice on a 1 cm$^2$ area.

Infection test: depilated mice on a 1 cm$^2$ area, where mild scarifications were made with a vaccinostyle.

Test product and treatment schedule: The protective foam was applied on the depilated area for a preventive treatment (applied amount not specified). The control animal did not receive any treatment.

Method of assessment: Preliminary test: research of Brucella on samples taken on skin with a cotton swab. Seeding an a solid albimi medium and incubation for 48 hours at 37° C.

Infection test: research of an infection using a culture of homogenised liver and spleen on a solid Albimi medium. Only one colony of Brucella in one of these organs was sufficient to confirm the infection of a mouse.

Results:

Preliminary test: 9 out of 10 control mice were infected by *Brucella melitenses.* 1 out of 10 treated mice were infected by *Brucella melitensis.*

Infection test: 8 out of 10 control mice were infected. None of the treated mice was infected

I claim:

1. A skin preparation comprising lipophilic and hydrophilic compounds suitable for application to the skin, which exists as a two-phase system which is capable of resulting in a semi-permeable membrane when applied to the skin, wherein said skin preparation is prepared by combination of about 5 to 8% by weight of a fatty acid comprising 14 to 20 carbon atoms, or a mixture of such fatty acids, about 0.73 to 2.66% of triethanolamine, about 4.5 to 7.0% of monopropylene glycol, about 1.5 to 1.97% of polyvinyl pyrrolidone, at most about 5.0% of dimethyl polysiloxane, and about 1 to 2% of at least one of glycerol, sorbitol, and polyethylene glycol, or a mixture thereof; and water, wherein the amount of water may comprise the balance of the preparation which totals 100%.

2. The skin preparation of claim 1, which is prepared by combination of 6.25% of at least one fatty acid comprising 14 to 20 carbon atoms as a mixture thereof, about 0.91% of triethanolamine, about 5.8% of monopropylene glycol, about 1.69% of polyvinyl pyrrolidone, about 0.5 to 0.95% of dimethyl polysiloxane, about 1.52% of at least one of glycerol, sorbitol, polyethylene glycol, or a mixture thereof, and water.

3. The skin preparation of claim 1, which further comprises a frothing agent.

4. The skin preparation of claim 3, wherein the amount of said frothing agent ranges from 1.3 to 3.7%.

5. The skin preparation of claim 4, wherein the amount of said frothing agent is about 1.5%.

6. The skin preparation of claim 1, which is in the form of a foam.

7. An aerosolic container which comprises the foam formulation of claim 6.

8. A method for preparing the skin preparation of claim 1, which comprises the following steps:

(a) dissolving and agitating in water at least one fatty acid comprising 14 to 20 carbon atoms or a mixture thereof in a vessel to produce solution A;

(b) dissolving and vigorously agitating in another vessel, water and polyvinyl pyrrolidone;

(c) adding to the vessel in step (b), during agitation, at least one of glycerol, sorbitol, polyethylene glycol, or mixture thereof, to produce solution B after a reaction time ($t_c$);

(d) adding said solution B to said vessel comprising solution A and allowing a reaction to occur during a reaction time ($t_d$); and (e) cooling the product that results from step (d) by the addition of cold water and, while agitating, adding dimethyl polysiloxane thereto to produce said skin preparation.

9. The method of claim 8, wherein at least one of step (a) and step (b) is effected at a temperature of at least about 80° C.

10. The method of claim 9, wherein at least one of step (a) and step (b) is effected at a temperature at least about 95° C.

11. The method of claim 8, wherein $t_c$ is about 30 minutes, and $t_d$ is about 60 minutes.

12. A method for or alleviating itching or skin irritation comprising topically applying to a subject in need of such treatment a skin preparation according to claim 1.

13. The method of claim 12, which is used to treat contact dermatitis or eczema.

14. The method of claim 12, wherein said skin preparation is topically applied in conjunction with at least one active substance.

15. The method of claim 14, wherein said active substance is a therapeutic or veterinary agent.

16. The method of claim 14, wherein said active substance is a light absorbing or filtering agent.

17. A method of alleviating infection of the skin comprising topically applying to an area in need of such treatment a skin preparation according to claim 1.

18. A method of alleviating allergic reaction to metal comprising topically applying an effective amount of a skin preparation according to claim 1 a subject in need of such treatment.

19. The method of claim 12, wherein said skin preparation is topically applied in conjunction with at least one active agent selected from the group consisting of a sunscreen, sun-filtering agent, anaesthetic, fungicidal agent, and bactericide.

20. The method of claim 12, wherein said skin preparation is topically applied repeatedly to a subject in need of such topical application.

* * * * *

UNITED STATES PATENT AND TRADEMARK OFFICE
CERTIFICATE OF CORRECTION

PATENT NO. : 5,993,830
DATED : November 30, 1999
INVENTOR(S) : Göran Freij

It is certified that error appears in the above-identified patent and that said Letters Patent is hereby corrected as shown below:

Column 8,
Lines 19 and 58, delete "propylene" and insert -- pyrrolidone --.

Column 9,
Line 23, delete "propylene" and insert -- pyrrolidone --.

Column 14,
Line 6, after "agitation," and before "at" insert -- monopropylene glycol, triethanolamine and --.

Signed and Sealed this

Eighth Day of April, 2003

JAMES E. ROGAN
*Director of the United States Patent and Trademark Office*